(12) United States Patent
Patience et al.

(10) Patent No.: US 9,540,590 B2
(45) Date of Patent: Jan. 10, 2017

(54) PROCESS AND SYSTEM FOR PRODUCING A FATTY ACID ALKYL ESTER

(71) Applicant: POLYVALOR LIMITED PARTNERSHIP, Montreal, Québec (CA)

(72) Inventors: Gregory Patience, Mount Royal (CA); Mahesh Edake, Montreal (CA); Cristian Neagoe, Longueuil (CA); Daria Camilla Boffito, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 14/894,429

(22) PCT Filed: May 29, 2014

(86) PCT No.: PCT/CA2014/050500
§ 371 (c)(1),
(2) Date: Nov. 27, 2015

(87) PCT Pub. No.: WO2014/190436
PCT Pub. Date: Dec. 4, 2014

(65) Prior Publication Data
US 2016/0108344 A1    Apr. 21, 2016

Related U.S. Application Data

(60) Provisional application No. 61/828,336, filed on May 29, 2013.

(51) Int. Cl.
| | | |
|---|---|---|
| *C11C 3/00* | (2006.01) | |
| *C11C 3/10* | (2006.01) | |
| *C11C 3/04* | (2006.01) | |
| *C07C 67/03* | (2006.01) | |
| *B01J 8/18* | (2006.01) | |

(Continued)

(52) U.S. Cl.
CPC ............... *C11C 3/10* (2013.01); *B01J 8/1836* (2013.01); *B01J 8/24* (2013.01); *C07C 67/03* (2013.01); *C10L 1/026* (2013.01); *C11C 3/04* (2013.01); *B01J 2208/00168* (2013.01); *B01J 2208/00902* (2013.01); *C10L 2200/0476* (2013.01); *C10L 2270/026* (2013.01); *C10L 2290/06* (2013.01); *Y02E 50/13* (2013.01)

(58) Field of Classification Search
CPC .............. C11C 3/10; C11C 3/04; C07C 67/03; C10L 1/023; B01J 8/1836; B01J 8/24
USPC ........................................................ 554/167
See application file for complete search history.

(56) References Cited

FOREIGN PATENT DOCUMENTS

| CA | 1247130 | 12/1988 |
| CA | 1247130 A1 * | 12/1988 |
| CA | 2637799 A1 | 8/2007 |

(Continued)

OTHER PUBLICATIONS

Barakos, N., Pasias, S and Papayannakos, N. "Transesterification of triglycerides in high and low quality oil feeds over an HT2 hydrotalcite catalyst". Bioresource Technology 99:5037-5042, 2008.

(Continued)

*Primary Examiner* — Deborah D Carr
(74) *Attorney, Agent, or Firm* — Isabelle Pelletier

(57) ABSTRACT

A process and a system for producing a fatty acid alkyl ester from an alcohol and a feedstock containing transesterifiable lipids are provided.

20 Claims, 5 Drawing Sheets

(51) Int. Cl.
*B01J 8/24* (2006.01)
*C10L 1/02* (2006.01)

(56) References Cited

FOREIGN PATENT DOCUMENTS

| CA | | 2637799 A1 * | 9/2007 | |
|---|---|---|---|---|
| NZ | WO | 2007049979 A1 * | 5/2007 | ............. C10L 1/026 |
| WO | | 2007049979 A1 | 5/2007 | |

OTHER PUBLICATIONS

Bruhns, Stefan and Werther, Joachim. "An investigation of the Mechanism of Liquid Injection into Fluidized Beds". AlChE Journal 51:766-775, 2005.
Xie, Wenlei, Peng, Hong and Chen, Ligong. "Calcined Mg—Al hydrotalcites as solid base catalysts for methanolyssis of soybean oil". Journal of Molecular Catalysis A: Chemical 246:24-32, 2006.
Zhen, Hong-yan, Feng, Zhen, Deng, Xin and Li, Yu-qin. "Activation of Mg—Al hydrocalcite catalysts for transesterification of rape oil" Fuel 87:3071-3076, 2008.
International Search Report and Written Opinion, PCT/CA2014/050500, Aug. 1, 2014.

\* cited by examiner

PROCESS AND SYSTEM FOR PRODUCING A FATTY ACID ALKYL ESTER

CROSS REFERENCE TO RELATED APPLICATIONS

This application is a National Entry Application of PCT application no PCT/CA2014/050500 filed on May 29, 2014 and published in English under PCT Article 21(2), which itself claims benefit of U.S. provisional application No. 61/828,336, filed on May 29, 2013. All documents above are incorporated herein in their entirety by reference.

FIELD OF THE INVENTION

The present invention relates to a process and a system for producing a fatty acid alkyl ester. More specifically, the present invention is concerned with a process and a system for producing a fatty acid alkyl ester through heterogeneous catalysis gas phase transesterification of glycerides.

BACKGROUND OF THE INVENTION

Biodiesel is a non-petroleum-based fuel made from renewable resources, for example, plants, microorganisms, or the like. It can be used as a diesel fuel substitute or as a component of fuel blends. Biodiesel is biodegradable and non-toxic, so fuel spills pose far less risk to the environment. Further, because the production of biodiesel "recycles" $CO_2$, biodiesel production and use does not significantly contribute to global warming.

Biofuels, and in particular biodiesel, are now produced in many countries as alternatives to petroleum products. Biodiesel is usually produced from a variety of oils, such as vegetable oils or recycled fryer oils, and waste animal fat. Biodiesel may be used alone or in mixture with petroleum diesel to fuel all types of vehicles equipped with diesel engines including trucks, locomotives, industrial equipment, private cars and boats. Biodiesel use reduces greenhouse gas emission and consequently many governments have promoted it through tax exemption and other various incentives. Therefore, several biodiesel production plants have been built throughout the world and more are planned to enter into production in the next few years.

Chemically, biodiesel feedstock can be composed primarily of transesterifiable lipids, including for example glycerides, which are formed from a single molecule of glycerol with one to three long chain fatty acids attached.

Biodiesel can be produced by direct transesterification of such lipids (including mono-, di-, or triglycerides) from an oil or a fat with an alcohol, often methanol, in presence of an acidic or basic catalyst:

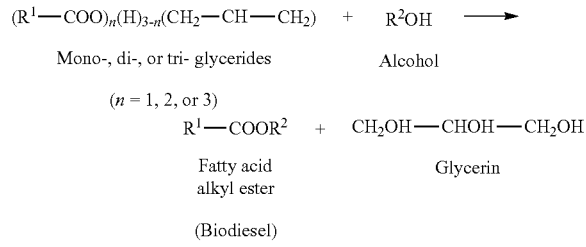

Several acidic or basic catalysts are known to be useful for this reaction.

SUMMARY OF THE INVENTION

In accordance with the present invention, there is provided:
1. A process for producing a fatty acid alkyl ester, the process comprising:
    (a) providing a gaseous alcohol and/or a gaseous ether, a gaseous feedstock containing transesterifiable lipids, and a solid catalyst,
    (b) in a reactor, contacting the gaseous alcohol and/or the gaseous ether, the gaseous feedstock, and the solid catalyst,
   wherein the contacting results in formation of a transesterified reaction product comprising the fatty acid alkyl ester.
2. The process of item 1, wherein the gaseous alcohol and/or the gaseous ether and/or the gaseous feedstock are provided by atomization of the alcohol and/or the ether and/or the feedstock, respectively, preferably by atomization of a liquid mixture of the feedstock with the alcohol and/or the ether.
3. The process of item 2, wherein the atomization is carried out using an atomizer nozzle and an inert atomization gas.
4. The process of item 3, wherein the atomization gas is carbon monoxide and/or dioxide, methane, ethane, water vapour, nitrogen, oxygen, nitrous oxides, hydrogen, ethylene, or a noble gas, preferably nitrogen or argon.
5. The process of any one of items 2 to 4, wherein the alcohol and/or the ether and/or the feedstock or the liquid mixture is heated before atomization.
6. The process of item 5, wherein the alcohol and/or the ether and/or the feedstock or the liquid mixture is at a temperature between about 25 and about 500° C., preferably between about 40 and about 70° C., before atomization.
7. The process of any one of items 1 to 6, wherein the alcohol is a $C_{1-6}$ aliphatic linear or branched alcohol optionally substituted by an aryl or heteroaryl group.
8. The process of item 7, wherein the alcohol is one or more of methanol, ethanol, propanol, butanol, hexanol, heptanol, octanol, nonanol, decanol, benzyl alcohol, iso-butyl alcohol, n-butyl alcohol, 2-ethyl hexanol, furfuryl alcohol, iso-propyl alcohol, or n-propyl alcohol, preferably methanol or ethanol, and more preferably methanol.
9. The process of any one of items 1 to 8, wherein the ether is a $C_{1-6}$ aliphatic linear, branched or cyclic ether optionally substituted by an aryl or heteroaryl group.
10. The process of item 9, wherein the ether is one or more of dimethyl ether or tetrahydrofuran.
11. The process of any one of items 1 to 10, wherein the feedstock comprises one or more of a plant gum, a plant oil, or an animal fat.
12. The process of item 11, wherein the plant gum comprises one or more of artichoke oil gum, canola oil gum, castor oil gum, Chinese tallow tree oil gum, coconut oil gum, corn oil gum, cottonseed oil gum, flaxseed oil gum, hemp oil gum, jatropha oil gum, jojoba oil gum, karanj oil gum, kukui nut oil gum, milk bush oil gum, pencil bush oil gum, mustard oil gum, neem oil gum, olive oil gum, palm oil gum, peanut oil gum, radish oil gum, rapeseed oil gum, rice bran oil gum, safflower oil gum, sesame oil gum, soybean oil gum, sunflower oil gum, and tung oil gum.

13. The process of item 11, wherein the plant oil comprises one or more of artichoke oil, canola oil, castor oil, Chinese tallow tree oil, coconut oil, corn oil, cottonseed oil, flaxseed oil, hemp oil, jatropha oil, jojoba oil, karanj oil, kukui nut oil, milk bush oil, pencil bush oil, mustard oil, neem oil, olive oil, palm oil, peanut oil, radish oil, rapeseed oil, rice bran oil, safflower oil, sesame oil, soybean oil, sunflower oil, and tung oil.

14. The process of item 11, wherein the animal fat comprises one or more of tallow, choice white grease (lard), and poultry fat.

15. The process of any one of items 1 to 14, wherein the transesterifiable lipids are mono-, di-, and tri-glycerides, free fatty acids, or phospholipids, preferably mono-, di-, and tri-glycerides, and more preferably triglycerides 16. The process of any one of items 1 to 15, wherein the alcohol, the ether and the feedstock are provided with a feedstock:alcohol/ether molar ratio between about 1:230 and about 1:2.3, preferably between about 1:115 and about 1:4.6.

17. The process of any one of items 1 to 16, wherein the feedstock is provided at a catalyst:oil feed rate ratio (g:ml/min) between about 50:1 and about 1:10, preferably ranging from about 10:1 to about 1:1.

18. The process of any one of items 1 to 17, wherein the solid catalyst is basic.

19. The process of any one of items 1 to 18, wherein the solid catalyst is MgO and CaO (unsupported or supported over alumina), a zeolite, fluidized catalytic cracking (FCC) catalyst, a hydrotalcite of Co, Mg, Al and/or other metals, a mixed metallic oxide of Mn, V, Ni, W, Ti, Zr, Si, and/or $Al_2O_3$, a functionalized or unfunctionalized perovskite, or a silica alumate, preferably $MgO/Al_2O_3$, $CaO/Al_2O_3$, Mg—Al hydrotalcite, or FCC catalyst.

20. The process of any one of items 1 to 19, wherein the reactor is at a temperature higher than 200° C., for example between about 300 and about 600° C., preferably between about 350 to 550° C., and more preferably between about 400 and 500° C.

21. The process of item any one of items 1 to 20, wherein the pressure in the reactor is at a pressure of 10 bar to about 0.1 bar, preferably between 3 bar and 0.5 bar, and more preferably between 0.8 bar and 2 bar.

22. The process of item any one of items 1 to 21, further comprising injecting an inert cooling gas in an upper part of the reactor.

23. The process of item 22, wherein the inert cooling gas is carbon monoxide and/or dioxide, methane, ethane, air, water vapour, nitrogen, or a noble gas, preferably air, nitrogen or argon.

24. The process of item 22 or 23, wherein the inert cooling gas is at a temperature between about 20 and about 100° C., preferably between about 25 and about 70° C., and more preferably between about 20 and about 40° C.

25. The process of any one of items 1 to 24, further comprising collecting the reaction product.

26. The process of any one of items 1 to 25, wherein the reaction product further comprises glycerol and/or unreacted alcohol and/or unreacted ether.

27. The process of any one of items 1 to 26, wherein the reaction product further comprises a hydrocarbon, an aldehyde, and/or an alcohol.

28. The process of item 26 or 27, further comprising isolating the fatty acid alkyl ester from the reaction product.

29. The process of item any one of items 1 to 28, wherein the fatty acid alkyl ester comprises a fatty acid methyl ester, a fatty acid ethyl ester, or a mixture thereof.

30. The process of any one of items 1 to 29, further comprising the step of regenerating the catalyst.

31. A system for producing a fatty acid alkyl ester from an alcohol and/or an ether and a feedstock containing transesterifiable lipids, the system comprising:
    (a) a heated fluidized bed reactor comprising a distributor supporting a solid catalyst,
    (b) an inert fluidization gas inlet located below the distributor for producing a fluidized bed of the solid catalyst above the distributor,
    (c) an atomizer nozzle located above the distributor and at the bottom of the fluidized bed, the nozzle being fed an inert atomization gas and a liquid mixture of the alcohol and/or ether and the feedstock, and
    (d) a transesterified reaction product gas outlet located above the fluidized bed.

32. The system of item 31, wherein the fluidization gas is carbon monoxide and/or dioxide, nitrogen, argon, water vapour or a mixture of oxygen and nitrogen, preferably nitrogen or argon.

33. The system of item 31 or 32, wherein the atomization gas is carbon monoxide and/or dioxide, methane, ethane, water vapour, nitrogen, or a noble gas, preferably nitrogen or argon.

34. The system of any one of items 31 to 34, further comprising an inert cooling gas inlet located between the fluidized bed and below the product gas outlet.

35. The system of item 34, wherein the cooling gas is carbon monoxide and/or dioxide, methane, ethane, air, water vapour, nitrogen, or a noble gas, preferably air, nitrogen or argon 36. The system of any one of items 31 to 35, further comprising one or more pump to feed the atomizer nozzle with the alcohol and/or the ether and the feedstock.

37. The system of any one of items 31 to 36, further comprising a furnace to heat the fluidized bed reactor.

38. The system of any one of items 31 to 37, further comprising a quench connected to the product gas outlet to collect the transesterified reaction product.

DETAILED DESCRIPTION OF THE INVENTION

Figure 1:
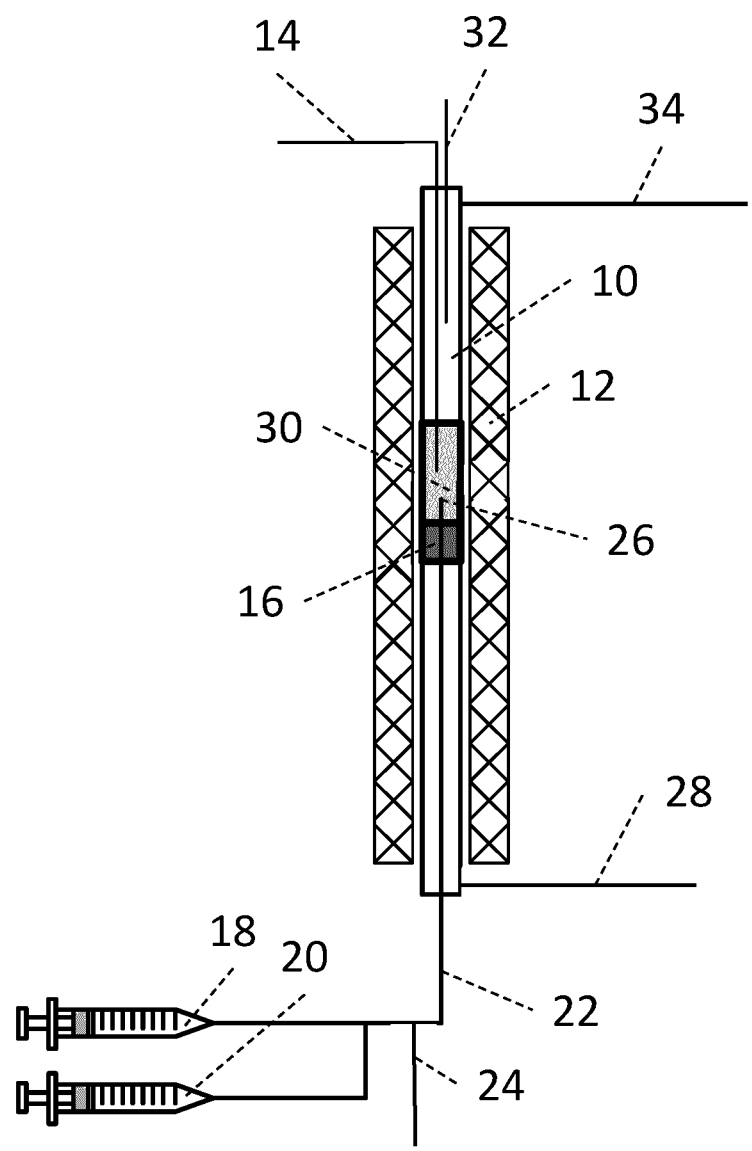
FIG. 1 is a scheme of a system according to an embodiment of the invention.

Process for Producing a Fatty Acid Alkyl Ester

Turning now to the invention in more details, there is provided a process for producing a fatty acid alkyl ester.

Herein, a fatty acid alkyl ester is a compound of formula $R^1$—$COOR^2$. In embodiments, $R^1$ is an aliphatic saturated or unsaturated linear or branched (preferably linear) chain comprising between 4 and 28 carbon atoms, preferably between 12 and 24 carbon atoms. In embodiments, $R^2$ is a linear or branched (preferably linear) alkyl chain comprising between 1 and 6 carbon atoms, preferably between 1 and 3 carbon atoms, more preferably 1 or 2 carbon atoms, and yet more preferably only one carbon atom. Colloquially, such long-chain alkyl esters and their mixtures are referred to as "biodiesel".

The process of the invention is based on the catalytic gas phase transesterification reaction of transesterifiable lipids contained in a feedstock with an alcohol and/or an ether in the presence of a heterogeneous (solid) catalyst to give fatty acid alkyl esters. Therefore, the process comprises the steps of providing a gaseous alcohol and/or a gaseous ether, a gaseous feedstock containing transesterifiable lipids, and a solid catalyst, and, in a reactor, contacting the gaseous alcohol and/or the gaseous ether, the gaseous feedstock, and the solid catalyst, wherein the contacting results in formation of a transesterified reaction product comprising the desired fatty acid alkyl ester. The reaction between the transesterifiable lipids and the alcohol/ether occurs in the gas phase and is catalyzed at the surface of the solid catalyst.

In embodiments, the alcohol is a $C_{1-6}$ aliphatic linear, branched or cyclic alcohol optionally substituted by an aryl or heteroaryl group. In embodiments, the alcohol is one or more of methanol, ethanol, propanol, butanol, hexanol, heptanol, octanol, nonanol, decanol, benzyl alcohol, iso-butyl alcohol, n-butyl alcohol, 2-ethyl hexanol, furfuryl alcohol, iso-propyl alcohol, or n-propyl alcohol. Preferably, the alcohol is methanol or ethanol, which produces fatty acid methyl esters and ethyl esters, respectively. More preferably, the alcohol is methanol.

In embodiments, the ether is a $C_{1-6}$ aliphatic linear, branched or cyclic ether optionally substituted by an aryl or heteroaryl group. In embodiments, the ether is one or more of dimethyl ether or tetrahydrofuran.

In embodiment, the gaseous alcohol and/or the gaseous ether is gaseous alcohol only.

In embodiments, the transesterifiable lipids in the feedstock are mono-, di-, and tri-glycerides, free fatty acids, or phospholipids, preferably mono-, di-, and tri-glycerides, and more preferably triglycerides. In embodiments, the feedstock comprises one or more of a plant oil gum, a plant oil, or an animal fat. This includes unused gums, oils and fats as well as used ones, for example waste cooking oil.

In embodiments, the plant gum comprises one or more of artichoke oil gum, canola oil gum, castor oil gum, Chinese tallow tree oil gum, coconut oil gum, corn oil gum, cottonseed oil gum, flaxseed oil gum, hemp oil gum, jatropha oil gum, jojoba oil gum, karanj oil gum, kukui nut oil gum, milk bush oil gum, pencil bush oil gum, mustard oil gum, neem oil gum, olive oil gum, palm oil gum, peanut oil gum, radish oil gum, rapeseed oil gum, rice bran oil gum, safflower oil gum, sesame oil gum, soybean oil gum, sunflower oil gum, and tung oil gum. In embodiments, the plant oil comprises one or more of artichoke oil, canola oil, castor oil, Chinese tallow tree oil, coconut oil, corn oil, cottonseed oil, flaxseed oil, hemp oil, jatropha oil, jojoba oil, karanj oil, kukui nut oil, milk bush oil, pencil bush oil, mustard oil, neem oil, olive oil, palm oil, peanut oil, radish oil, rapeseed oil, rice bran oil, safflower oil, sesame oil, soybean oil, sunflower oil, and tung oil. In embodiments, the animal fat comprises one or more of tallow, choice white grease (lard), and poultry fat.

In embodiments, the alcohol/ether and the feedstock are provided with a feedstock:alcohol/ether flow ratio between about 1:10 and about 10:1, preferably between about 1:5 and about 5:1. This corresponds to feedstock:alcohol/ether molar ratios between about 1:230 and about 1:2.3, preferably between about 1:115 and about 1:4.6. A molar excess of alcohol/ether will typically shift the reaction equilibrium toward the desired direction, e.g. toward the fatty acid alkyl ester side of the reaction, and thus likely improve the yield.

In embodiments, the feedstock is provided at a catalyst:oil feed rate ratio (g:ml/min) between about 50:1 and about 1:10, preferably between about 10:1 and about 1:1. Catalyst deactivation rates will typically decrease with increasing catalyst:oil feed ratios. However, as a consequence, the reactor volumes will typically increase, while the oil/oxygen cycle will increase. In other words, the use of greater amounts of catalyst typically increases the time it takes to coke and deactivate the catalyst.

The catalyst is in solid form. As such, the reaction will take place between the gaseous alcohol/ether and the gaseous feedstock when adsorbed at the surface of the solid catalyst particles. In embodiment, the catalyst may be basic, acidic or bi-functional. In embodiments, the catalyst is a heterogeneous acidic or basic catalyst. Non-limiting examples of catalysts include MgO and CaO (unsupported or supported over alumina), zeolites, fluidized catalytic cracking (FCC) catalyst (a type Y zeolite), hydrotalcites (of Co, Mg, Al and/or other metals), mixed metallic oxides (for example of Mn, V, Ni, W, Ti, Zr, Si, $Al_2O_3$), functionalized (sulphated, fluorinated) and unfunctionalized perovskites, and silica alumates. In preferred embodiments, the catalyst is basic. For example, the catalyst can be, in embodiments, $MgO/Al_2O_3$, $CaO/Al_2O_3$, Mg—Al hydrotalcite, or fluidized catalytic cracking (FCC) catalyst. The present inventors observed that Mg—Al hydrotalcite was highly active when the alcohol was ethanol and methanol.

The catalyst should resist mechanical stress and be compatible with catalyst regeneration. Such regeneration may be necessary as coking can take place during the reaction. Catalyst regeneration can be carried with air or any other oxidizing environment (for example $O_2/N_2$, $N_2O$, $NO_2$, CO, etc.). The frequency of catalyst regeneration will depend on the nature of catalyst. Some of the catalysts can operate with a longer contact time with the oil feed while maintaining high conversion. Long contact times thus correspond to a low frequency required to regenerate the catalyst with an oxidant. In general, higher frequencies are needed for FCC, while lower frequencies are suitable for hydrotalcite, MgO and CaO. Catalyst contact in oil may generally range from about 5 seconds to about 120 minutes, preferably from about 30 seconds and about 20 minutes. For example, it can range from as little as 5 seconds to 10 minutes, more preferably from 20 seconds to 5 minutes for FCC. For hydrotalcite, MgO and CaO, it may range from 10 seconds to 40 minutes, more preferably from 1 minute to 20 minutes. The duration of catalyst regeneration will depend on the nature of the catalyst, the degree of coking and the partial pressure of the oxidant. Catalyst regeneration can last from 30 seconds to 30 minutes, more preferably from 1 minute to 10 minutes.

In embodiments, either or both of the gaseous alcohol/ether and the gaseous feedstock are provided in the reactor by atomization. Herein, "atomization" is the making of an aerosol, which is a colloid suspension of fine liquid droplets in a gas. Atomization can be carried out using an atomizer nozzle, which is an aspirator nozzle using the Venturi effect to produce a fine spray of a liquid. The operation of such a nozzle rests on the fact that when a gas is injected under pressure through a tube with a decreasing section, it speeds up, generating a pressure drop at the narrowest point due to Bernoulli's principle. Thus, atomization of the alcohol/ether in liquid form, the feedstock in liquid form, or of a liquid mixture thereof, using an inert gas (referred herein as the atomization gas) will produce fine droplets of the alcohol/ether, the feedstock, or the liquid mixture, respectively, in the reactor. Under typical reaction conditions (i.e. temperatures higher than the boiling points of the alcohol/ether and feedstock), these droplets will rapidly vaporize thus providing the desired gaseous alcohol/ether and gaseous feedstock and/or will contact the catalyst, at least partly react on its surface, and subsequently vaporize.

The atomization gas can be any inert gas. In embodiments, the inert atomization gas is carbon monoxide and/or dioxide, methane, ethane, water vapour, nitrogen, oxygen, nitrous oxides, hydrogen, ethylene, or a noble gas. Preferably, the atomization gas is nitrogen or argon.

In preferred embodiments, the gaseous alcohol/ether and the gaseous feedstock are provided in the reactor by atomization of a liquid mixture of the feedstock with the alcohol/ether.

In embodiments, this liquid mixture, the feedstock and/or the alcohol/ether, may be heated before atomization. Heating typically decreases the viscosity and the superficial tension of the liquid mixture and reduces the heat load on the reactor. More specifically, they can be heated to a temperature between about 25 and about 500° C., preferably between about 40 and about 70° C.

The temperature of the reactor should be sufficient to prevent a liquid phase from forming. In embodiments, the reactor is at a temperature higher than 200° C., for example between about 300 and about 600° C., preferably between about 350 to 550° C., and more preferably between about 400 and 500° C. The temperature would of course be adjusted depending on the nature of the catalyst used and the feedstock:alcohol/ether ratio. Increasing temperature will typically increase the reaction rates and possibly reduce the amount of coke formed. Higher temperatures will also generally increase the cracking rate of the biodiesel formed and possibly the oil. This would result in a lower molecular weight product that could potentially have a lower cold flow filter temperature. Higher temperatures may also produce light gases such as methane, ethane and the like. This would represent a yield loss of the bio-fuel, but could also become a valuable product.

Therefore, by adjusting the reaction conditions, the production of one or more secondary products can be lowered or increased as desired. The secondary products include the products of cracking of the biodiesel and/oil as well as the above light gases. Therefore, in embodiments, the reaction product further comprises a hydrocarbon, an aldehyde, and/or an alcohol. These would include $C_{1-14}$ hydrocarbon, aldehydes, and alcohol, linear, branched, or cyclic, saturated or unsaturated (e.g. paraffins and olefins).

In embodiments, the pressure in the reactor is at a pressure of 10 bar to about 0.1 bar, preferably between 3 bar and 0.5 bar, and more preferably between 0.8 bar and 2 bar. Operating at lower pressure will typically allow the reaction to proceed at lower temperatures and thus reduce cracking reactions producing light organic gases, CO and $CO_2$.

In embodiments, the process further comprises injecting an inert cooling gas in an upper part of the reactor. This gas decreases the temperature in this part of reactor, which typically decreases the decomposition of glycerol and other products. This further beneficially reduces the partial pressure of glycerol. The cooling gas can be any inert gas. In embodiments, the cooling gas is carbon monoxide and/or dioxide, methane, ethane, air, water vapour, nitrogen, or a noble gas. Preferably, the cooling gas is air, nitrogen or argon. In embodiments, the inert cooling gas is at a temperature between about 20 and about 100° C., preferably between about 25 and about 70° C., and more preferably between about 25 and about 40° C.

In embodiments, the fatty acid alkyl ester produced by the above process comprises a fatty acid methyl ester, a fatty acid ethyl ester, or a mixture thereof. In embodiments, the process further comprises the step of collecting the reaction product. This may include for example, passing the gas effluent through a quench. This reaction product comprises the desired fatty acid alkyl ester and may further comprise glycerol and/or unreacted alcohol. Thus, in embodiments, the process further comprises isolating the fatty acid alkyl ester from the reaction product. This may be achieved by known methods, for example decantation, extraction, and distillation.

In embodiments, the process of the invention is carried out using a system and reactor as described herein below.

System for Producing a Fatty Acid Alkyl Ester

In another aspect of the invention, there is provided a system that can be used to carry the above process.

There is thus provided a system for producing a fatty acid alkyl ester from an alcohol and/or an ether and a feedstock containing transesterifiable lipids. This system comprises a heated fluidized bed reactor comprising a distributor supporting a solid catalyst.

A fluidized bed reactor is a reactor typically used to carry out multiphase chemical reactions. In this type of reactor, a fluid (a fluidization gas in the present case) is passed through a granular solid material (catalyst particles in the present case) at high enough velocities to suspend the solid and cause it to behave as though it were a fluid. This process is known as fluidization. The solid material in the fluidized bed reactor is supported by a porous distributor. The fluidization gas is forced through the distributor up through the solid material. The fluidization gas can be any inert gas. In embodiments, the fluidization gas is carbon monoxide and/or dioxide, nitrogen, argon, water vapour or a mixture of oxygen and nitrogen, preferably nitrogen or argon. The fluidization gas flow rate will vary depending on the design and size of the reactor. It may vary, for example, between about 40 mL/min and about 70 mL/min. In a commercial embodiment, the gas feed rate to the reactor will be sufficient to maintain the solids fluidized. Thus, it would be maintained at a gas velocity greater than the minimum fluidization velocity. This velocity is typically as low as 2 mm/s for FCC catalyst and can be as high as 10 mm/s or even higher for other catalysts.

The fluidized bed reactor can be heated using any means known to the skilled person. In embodiments, the system further comprises a furnace, for example a tubular furnace if the reactor is tubular, to heat the fluidized bed reactor. The temperature of the reactor (especially that of the fluidized bed) should be sufficient to prevent a liquid phase from forming (which would result in a slurry reactor). In embodiments, the fluidized bed is at a temperature higher than 200° C., for example between about 300 and about 600° C., preferably between about 350 to 550° C., and more preferably between about 400 and 500° C.

The system also comprises an inert fluidization gas inlet located below the distributor for producing, as described above, a fluidized bed of the solid catalyst. This fluidized bed is located above the distributor and extends upward from the distributor for a certain distance, for example from as little as 2.5 cm to between about 10 to about 30 cm. In a commercial scale reactor, the fluidized bed extends upwards from the distributor to distances as high as 10 m.

The system also comprises an atomizer nozzle located above the distributor and at the bottom of the fluidized bed. This nozzle is fed an inert atomization gas and a liquid mixture of the alcohol/ether and the feedstock. As explained above, atomization of the liquid mixture using an inert atomization gas will produce fine droplets of the liquid mixture in the reactor. The atomization gas can be any inert gas. In embodiments, the inert atomization gas is carbon monoxide and/or dioxide, methane, ethane, water vapour, nitrogen, or a noble gas. Preferably, the atomization gas is nitrogen or argon. Because of its location, the nozzle beneficially forms a spray directly inside the fluidized bed of catalyst particles. The fluidized bed being at high temperature (because the reactor is heated), the droplets formed by atomization evaporate quickly and, very desirably, in the presence of the catalyst. This reduces the tendency of the solid to agglomerate and thus improves the contact efficiency with active sites.

The nozzle can be fed the atomization gas, the alcohol/ether, and the feedstock by any means known to the skilled person. In embodiments, the system further comprises one or more pump to feed the atomizer nozzle with the alcohol/ether and the feedstock. In embodiments, the system comprises one pump to feed the atomizer nozzle with the alcohol/ether and another pump to feed the atomizer nozzle with the feedstock. In embodiments, the alcohol/ether and the feedstock are provided with a feedstock:alcohol/ether flow ratio between about 1:10 and about 10:1, preferably between about 1:5 and about 5:1. This corresponds to feedstock:alcohol/ether molar ratios between about 1:230 and about 1:2.3, preferably between about 1:115 and about 1:4.6. In embodiments, the feedstock is provided at a catalyst:oil feed rate ratio (g:ml/min) between about 50:1 and about 1:10, preferably between about 10:1 and about 1:1.

The atomization gas flow can vary according to the liquid mixture feed rate. For example, the atomization gas flow can be between about 100 mL/min and about 500 mL/min, while the liquid mixture feed rate can be between about 0.1 and about 1 mL/min. The liquid mixture feed rate should not be excessive lest a liquid phase will form (which would result in a slurry reactor).

Prior to atomization, the liquid mixture can be heated using any means known to the skilled person. In embodiments, the liquid mixture is heated using hot gas produced by the transesterification reaction, the condensed liquid product of the transesterification reaction, or any other waste heat, such as condensed water vapour or steam.

The system also comprises a transesterified reaction product gas outlet located above the fluidized bed. This outlet allows the reaction product to exit the reactor. This transesterified reaction product comprises the desired fatty acid alkyl ester. It may also comprise glycerol and unreacted alcohol/ether as described above.

The transesterified reaction product exiting the reactor can be collected by any means known to the skilled person. In embodiments, a quench is connected to the product gas outlet to condense and collect the transesterified reaction product (mainly the desired fatty acid alkyl esters in alcohol/ether).

In embodiments, the system further comprises an inert cooling gas inlet located between the fluidized bed and the product gas outlet, preferably just above the fluidized bed. This inlet allows injection an inert cooling gas in the reactor, which will have the effects described above. The cooling gas can be any inert gas. In embodiments, the cooling gas is carbon monoxide and/or dioxide, methane, ethane, air, water vapour, nitrogen, or a noble gas. Preferably, the cooling gas is air, nitrogen or argon. The cooling gas flow rate will vary depending on the design and size of the reactor. It may vary, for example, between about 6 mL/min and about 20 mL/min.

All gas flows in the above system can be controlled, for example, by mass flow controllers.

FIG. 1 shows an embodiment of a system according to the invention. The system shown in FIG. 1 comprises a tube (10), for example a glass or quartz tube, for example with an internal diameter of 0.7 cm, enclosed in a tubular furnace (12). The temperature of the fluidized bed can be monitored using a thermocouple (14). A glass wool distributor (16) divides the quartz tube into two parts. The catalyst is supported by a distributor (16), for example, a glass wool distributor. Syringe pumps (18 and 20) feed the alcohol/ether and the feedstock for the reaction, respectively, to a sparger line (22), which is also fed with an inert atomization gas (24). This liquid mixture is then fed into the reactor via a vertical atomizer nozzle (26) located right above distributor (16). An inert fluidization gas (28) is also fed into the reactor, but below the distributor (16). This fluidization gas allows forming a fluidized bed (30). The alcohol/ether /oil mixture is thus atomized at the bottom of the fluidized bed (30). An inert cooling gas (32) is fed above the fluidized bed (30). Exhaust (34) allows collecting the gaseous products of the reaction.

Advantages of the Process and System of the Invention

Typically, transesterification reactions are carried out in the liquid phase at rather low temperatures. Such liquid phase heterogeneous catalytic transesterification reactions in batch reactors have indeed been reported at temperatures in the range of 60° C. to 200° C. It typically comprises the formation of alkoxides and subsequent alcoholysis. As shown herein, the gas-solids heterogeneous catalysis reaction of the process of the invention occurs at higher temperatures and has the potential to produce highly valued chemicals while reducing the number of process steps. As shown below, the process of the invention has been successfully used to produce a high quality biodiesel by transesterifying a vegetable oil over Mg—Al hydrotalcite and other catalysts in a fluidized bed.

Liquid-solids heterogeneous catalysis has been practiced for many years. However, mass transfer limitations, low reaction rates, and separating catalyst from the product are some of the common limitations of this process. It is shown herein that these limitations may be minimized by operating in the gas phase—vaporizing the liquid and simultaneously contacting it with solid catalyst.

In embodiments, the gas phase catalytic transesterification reaction of the process of the invention may have the following advantages over conventional liquid phase transesterification reactions:

1) Higher through put rates—higher reaction rates,
2) Higher selectivity,
3) High quality of products,
4) Superior economics, 5) Better temperature control in the reactor,
6) Continuous use of catalyst (no need to recover or dispose),
7) Smaller pressure drop (in a fluidized bed reactor compared to a fix bed reactor), and/or
8) Smaller resistance to diffusion through the particles (in a fluidized bed reactor compared to a fix bed reactor).

Definitions

Herein, the inert gases, such as the atomization gas, the cooling gas, and the fluidization gas, are gases that will not interfere with the reactants, products, and catalysts with which they will each come into contact. Exemplary gases have been listed above; however these lists are not exhaustive. Further, it should be understood that the gas listed do not need to be pure. Finally, it is envisioned and encompassed by the present invention to use recycle gas as any of the inert gases. Such recycle gas could contain carbon monoxide and/or dioxide, probably with one or more organic gases, with perhaps some nitrogen.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENT

The present invention is illustrated in further details by the following non-limiting examples.

Example 1

Experiments have been performed in the fluidized bed reactor shown in FIG. 1. In these experiments, the results of which are reported in the table below, the alcohol was methanol and the feedstock was canola oil. The atomization gas, the fluidization gas and the cooling gas were argon. The sparger line and cooling gas were at room temperature.

The product was condensed and collected using a quench. Its chemical composition was analysed by GC-FID. FIGS. 2 to 5 show the GC-FID spectra of the product obtained in the conditions listed in the table below. The internal standard used for GC-FID analysis was methyl nonadecanoate, while toluene was the diluting solvent.

Figure 2:
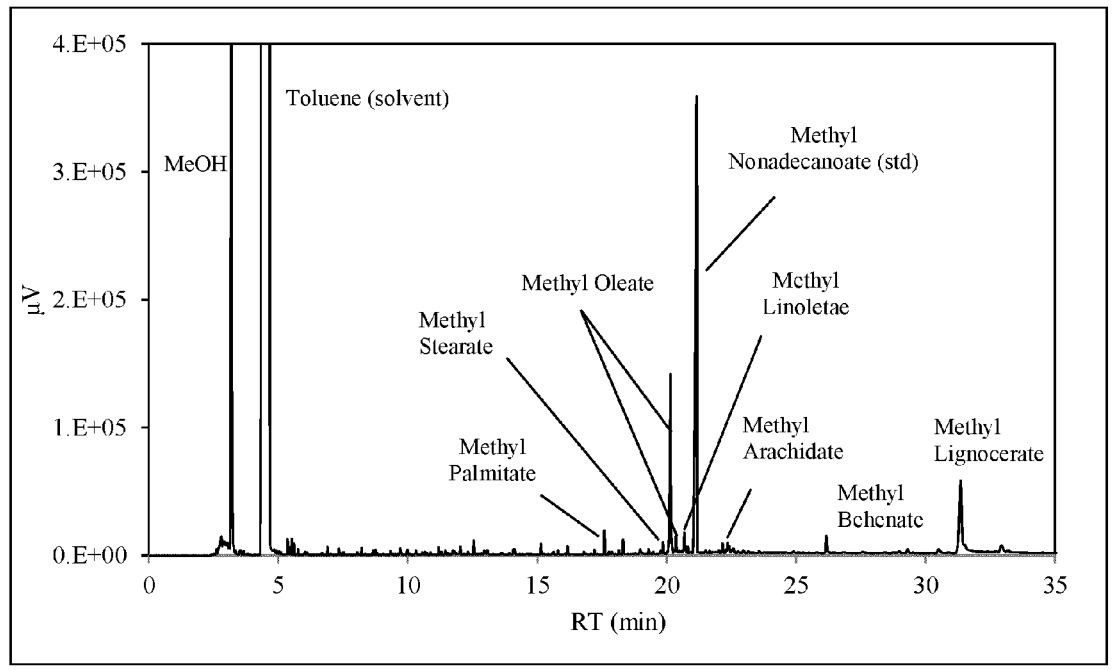
FIG. 2 is a GC-FID spectra of the product obtained in Example 1 using $MgO/Al_2O_3$ as a catalyst.
Figure 3:
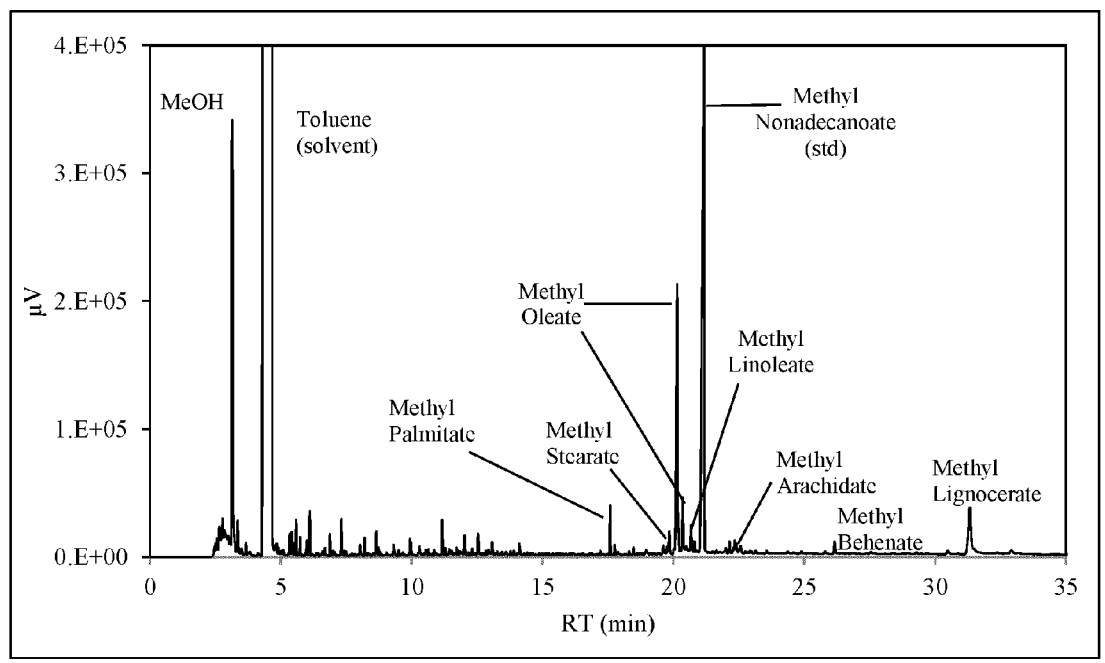
FIG. 3 is a GC-FID spectra of the product obtained in Example 1 using $CaO/Al_2O_3$ as a catalyst.
Figure 4:
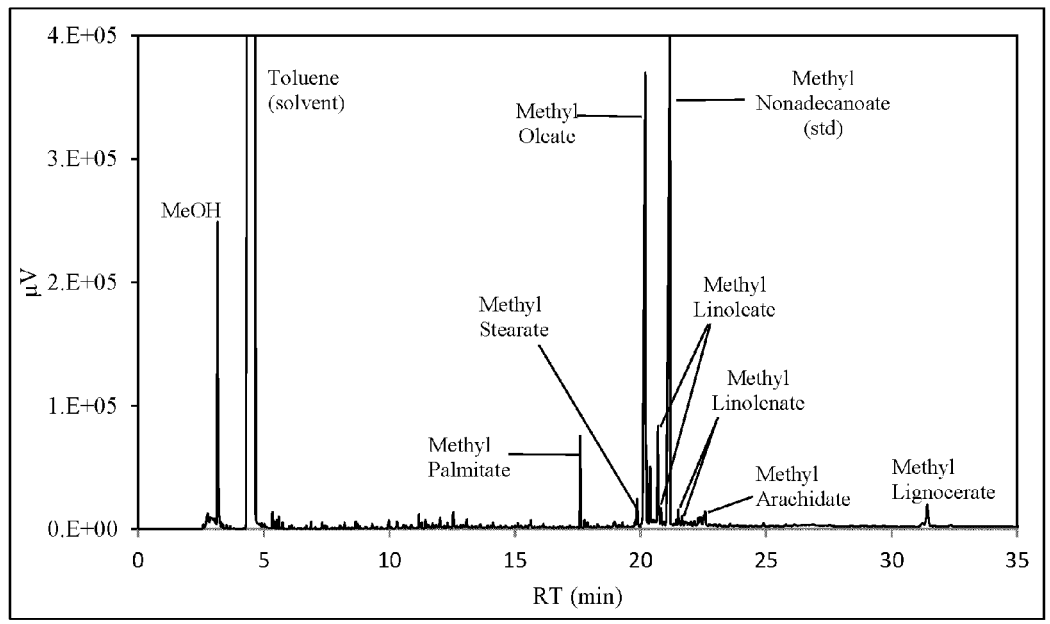
FIG. 4 is a GC-FID spectra of the product obtained in Example 1 using Mg—Al Hydrotalcite as a catalyst.
Figure 5:
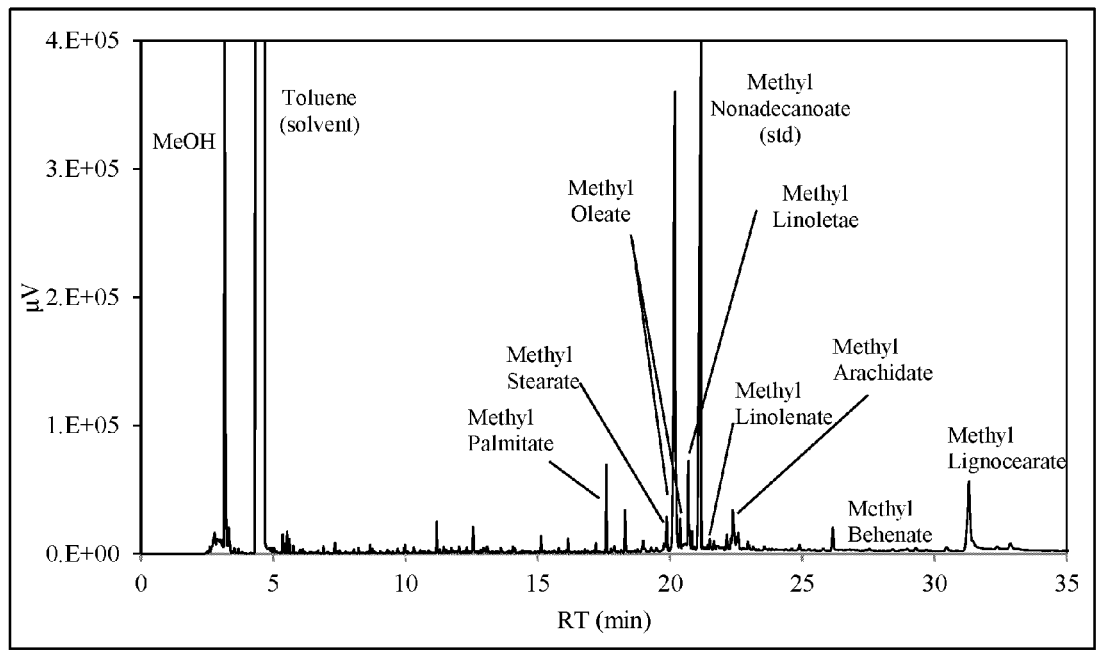
FIG. 5 is a GC-FID spectra of the product obtained in Example 1 using Fluidized catalytic cracking (FCC) catalyst.

|  | FIG. 2 | FIG. 3 | FIG. 4 | FIG. 5 |
| --- | --- | --- | --- | --- |
| Catalyst | $MgO/Al_2O_3$ | $CaO/Al_2O_3$ | Mg—Al Hydrotalcite | Fluidized catalytic cracking (FCC) catalyst |
| Flow Oil | 0.05 ml/min | 0.1 ml/min | 0.05 ml/min | 0.05 ml/min |
| Flow MeOH | 0.05 ml/min | 0.1 ml/min | 0.1 ml/min | 0.05 ml/min |
| Fluidization gas flow | 40 ml/min | 40 ml/min | 60 ml/min | 60 ml/min |
| Atomization gas flow | 12 ml/min | 12 ml/min | 12 ml/min | 12 ml/min |
| Cooling gas flow | 12 ml/min | 12 ml/min | 12 ml/min | 12 ml/min |
| Reaction Time | 16 min | 32 min | 90 min | 33.5 min |
| Reaction Temperature | 450° C. | 450° C. | 450° C. | 500° C. |
| Yield of biodiesel | 23.6% | 21.0% | 62.9% | 49.7% |

The GC-FID analysis shows a range of fatty acid alkyl esters. Traces of pigments and benzene derivatives were also observed. The unidentified peaks in these spectra are assumed to be due to hydrocarbons. The obtained biodiesel product has high purity.

Other experiments were carried out varying the following parameters:

| | |
| --- | --- |
| the flow rate of the atomization gas: | from 100 to 500 mL/min, |
| the feed rate of the liquid mixture: | from 0.1 to 1 mL/min, |
| the oil:alcohol molar ratios: | from 1:6 to 1:27, |
| the flow rate of the fluidization gas: | from 40 to 70 mL/min, |
| the flow rate of the cooling gas: | from 6 to 20 mL/min, and |

The data in the table above shows the highest yield for the Mg—Al hydrotalcite at 62.9% followed by the FCC catalyst at almost 50%. These yields depend on many parameters such as quantity of methanol, temperature, flow rate, catalyst, etc. Another factor was the time the catalyst had been in contact with the alcohol and feedstock. The highest bio-fuel production rates were obtained right after catalyst regeneration. As time went on, the production rates decreased.

Example 2

Further experiments have been performed. These experiments were carried out in a set-up similar to that described in Example 1. Successive cycles of reaction and regeneration were carried out in the following conditions:
Catalyst: 10% CaO/Al$_2$O$_3$, 0.6 g
Oil flow: 0.05 mL/min
MeOH flow: 0.1 mL/min
Total oil (in the whole experiment): 0.92 mL
Total MeOH (in the whole experiment): 1.66 mL
Atomization gas flow: Argon, 40 mL/min
Purge: Argon, 40 mL/min, no injection of oil and MeOH, before and after each stage (reaction and regeneration)
Regeneration: 33% vol O$_2$ in Argon, 60 mL/min, no injection of oil and MeOH
Temperature: 450° C.
No cooling gas flow The results are reported in the table below. Note that the reaction time, regeneration time, and purge time refer to time taken by each of these steps in a single cycle. Such cycles were repeated for the number of cycles indicated, giving the total experimental time reported. In all the cases the amount of MeOH and oil were the same.

|  | Experiment no. | | | | | | | | |
| --- | --- | --- | --- | --- | --- | --- | --- | --- | --- |
|  | 1 | 2 | 3 | 4 | 5 | 6 | 7 | 8 | 9 |
| Reaction time MeOH + oil, min | 1 | 1 | 1 | 2 | 2 | 2 | 5 | 5 | 5 |
| Regeneration time, min | 2 | 1 | 5 | 5 | 2 | 1 | 2 | 1 | 5 |
| Purge time, min | 0.5 | 0.5 | 0.5 | 0.5 | 0.5 | 0.5 | 0.5 | 0.5 | 0.5 |
| Number of cycles | 20 | 20 | 20 | 10 | 10 | 10 | 4 | 4 | 4 |
| Total experiment time, min | 71 | 51 | 131 | 76 | 46 | 36 | 31 | 27 | 43 |
| ME (biodiesel) yield (%) | 2.7 | 4.9 | 2.1 | 5.7 | 16.2 | 18.1 | 15.2 | 44.3 | 26.3 |
| Max amount of coke on the catalyst (% mol) | 8.7 | 4.9 | 14 | 11 | 5.1 | 3.0 | 2.6 | 8.1 | 5.1 |

It was observed that the temperature increased regularly during each regeneration cycle and then decreased after a couple of minutes, indicating the end of the regeneration step (there is other carbon on the catalyst that requires higher temperatures and/or more than 2 minutes to combust).

The resulting liquid was analyzed in a GC-FID and GC-MS. The amount of ME (biodiesel) reported in the above table was calculated from GC-FID chromatograms.

The GC-FID chromatograms were very similar to those obtained in Example 1. So none of them are provided here.

Figure 6:
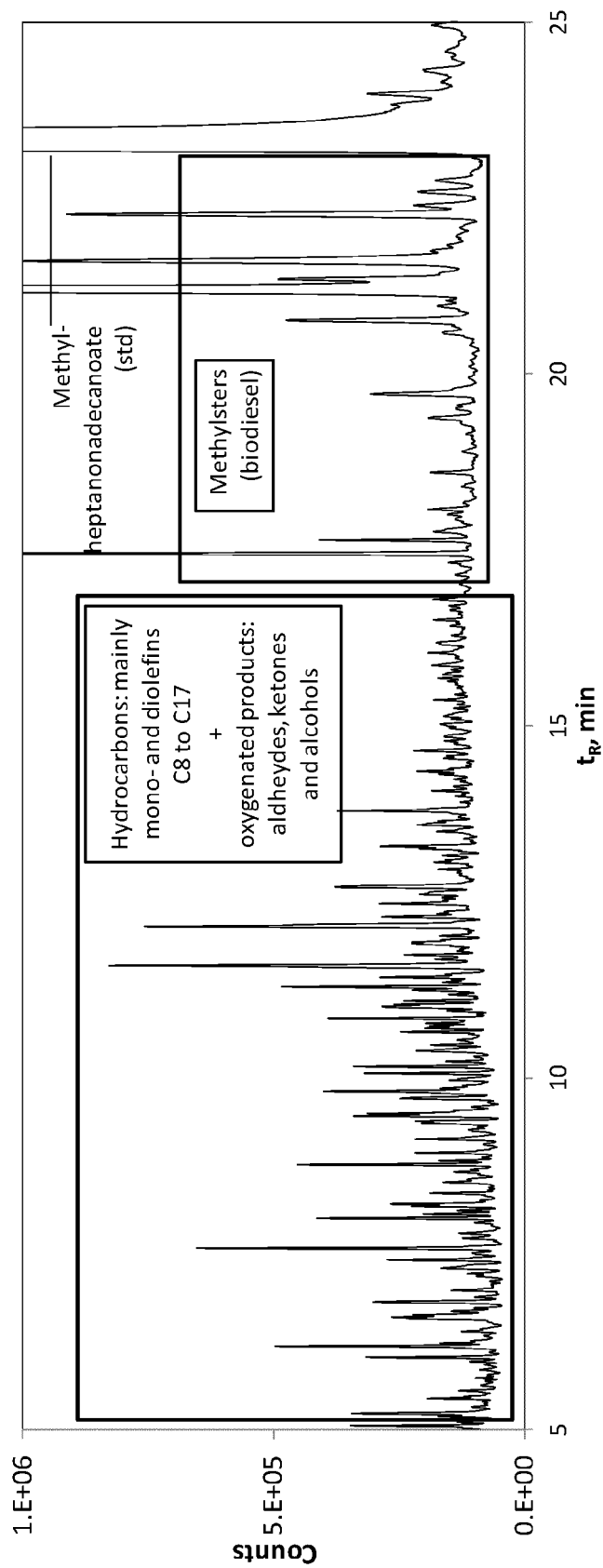
FIG. 6 is a GC-MS chromatogram of the product obtained in experiment 7 of Example 2.

The GC-MS chromatograms were all very similar to the one another. Only one of them is provided here (FIG. 6).

Figure 7:
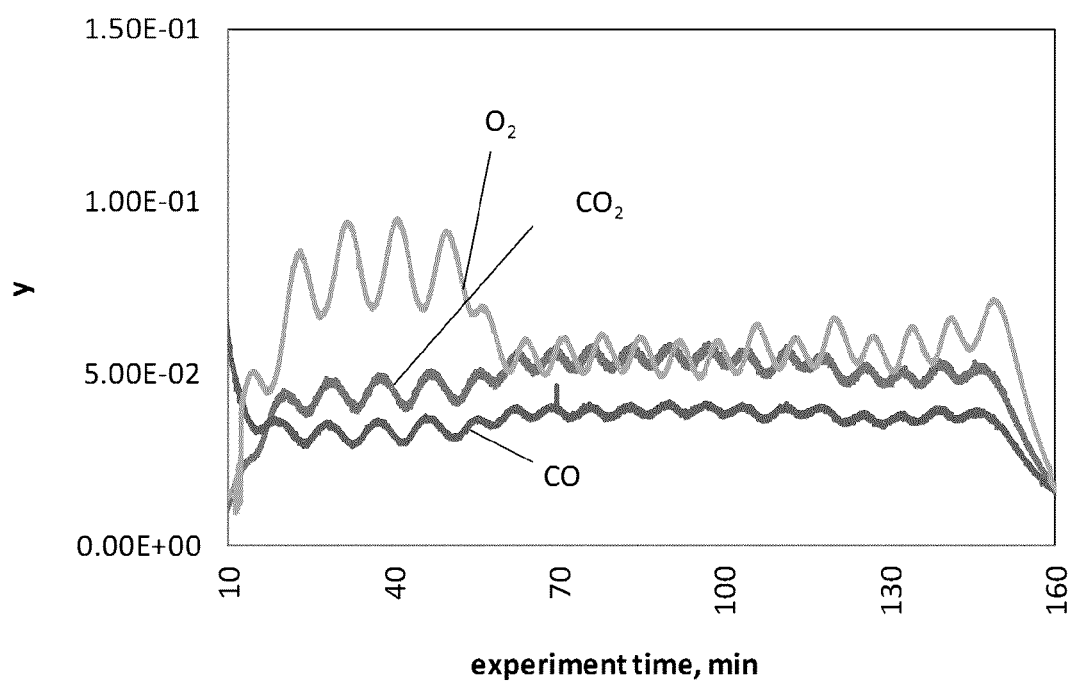
FIG. 7 is a MS trace of the product obtained in of experiment 4 of Example 2.

The gases out-flowing from the reactor were analyzed by a mass spectrometer (MS) and all had a similar profile. One such MS trace is provided here (FIG. 7).

About the C mass balance. The coke on the catalyst was calculated basing on the amount of CO and CO$_2$ evolved during regeneration and reaction cycles of each experiment. However, part of CO and CO$_2$ comes from the decarbonylation and decarboxylation of the triglycerides during the reaction cycle at which time paraffins and olefins form.

Based on the data, it was concluded that the more the catalyst is regenerated, the more cracking will occur and, as a consequence, the catalyst will be more active towards cracking (and more prone to coke) during the subsequent reaction cycle(s). Therefore, the more the catalyst is regenerated, the less methyl ester are obtained and more hydrocarbons (olefins, paraffins), oxygenated compounds and coke form.

The carbon balance is given by methyl esters (biodiesel, in the table)+coke (in the table)+paraffins+olefins+oxygenated compounds (aldehydes, ketones and alcohols). Among the hydrocarbons, the ones that are most prevalent in all the samples are mono and di-olefins C8-C17.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

N. Barakos, S. Pasias, N. Papayannakos, "Transesterification of triglycerides in high and low quality oil feeds over an HT2 hydrotalcite catalyst" Bioresource Technology, Volume 99, Issue 11, July 2008, Pages 5037-5042.

Wenlei Xie, Hong Peng, Ligong Chen, "Calcined Mg—Al hydrotalcites as solid base catalysts for methanolysis of soybean oil" Journal of Molecular Catalysis A: Chemical, Volume 246, Issues 1-2, 1 Mar. 2006, Pages 24-32.

Hong-yan Zeng, Zhen Feng, Xin Deng, Yu-qin Li "Activation of Mg—Al hydrotalcite catalysts for transesterification of rape oil " Fuel, Volume 87, Issues 13-14, October 2008, Pages 3071-3076

Stefen Bruhns, Joachim Werher, "An investigation of the mechanism of liquid injection into fluidized beds" Particle Technology and Fluidization" Volume, Issues 3, March 2005, pages 766-775.

The invention claimed is:

1. A process for producing a fatty acid alkyl ester, the process comprising:
    (a) providing a gaseous alcohol and/or a gaseous ether, a gaseous feedstock containing transesterifiable lipids, and a solid catalyst,
    (b) in a reactor, contacting the gaseous alcohol and/or the gaseous ether, the gaseous feedstock, and the solid catalyst,
wherein the contacting results in formation of a transesterified reaction product comprising the fatty acid alkyl ester.

2. The process of claim 1, wherein the gaseous alcohol and/or the gaseous ether and/or the gaseous feedstock are provided by atomization of the alcohol and/or the ether and/or the feedstock, respectively.

3. The process of claim 2, wherein the atomization is carried out using an atomizer nozzle and an inert atomization gas.

4. The process of claim 2, wherein the alcohol and/or the ether and/or the feedstock or the liquid mixture is heated before atomization.

5. The process of claim 4, wherein the alcohol and/or the ether and/or the feedstock or the liquid mixture is at a temperature between about 25 and about 500° C. before atomization.

6. The process of claim 1, wherein the alcohol, the ether and the feedstock are provided with a feedstock:alcohol/ether molar ratio between about 1:230 and about 1:2.3.

7. The process of claim 1, wherein the feedstock is provided at a catalyst:oil feed rate ratio (g:ml/min) between about 50:1 and about 1:10.

8. The process of claim 1, wherein the reactor is at a temperature higher than 200° C.

9. The process of claim 1, wherein the pressure in the reactor is at a pressure of 10 bar to about 0.1 bar.

10. The process of claim 1, further comprising injecting an inert cooling gas in an upper part of the reactor.

11. The process of claim 10, wherein the inert cooling gas is at a temperature between about 20 and about 100° C.

12. The process of claim 1, wherein the reaction product further comprises glycerol and/or unreacted alcohol and/or unreacted ether.

13. The process of claim 1, wherein the reaction product further comprises a hydrocarbon, an aldehyde, and/or an alcohol.

14. The process of claim 1, further comprising isolating the fatty acid alkyl ester from the reaction product.

15. The process of claim 1, wherein the fatty acid alkyl ester comprises a fatty acid methyl ester, a fatty acid ethyl ester, or a mixture thereof.

16. The process of claim 1, further comprising the step of regenerating the catalyst.

17. A system for producing a fatty acid alkyl ester from an alcohol and/or an ether and a feedstock containing transesterifiable lipids, the system comprising:
 (a) a heated fluidized bed reactor comprising a distributor supporting a solid catalyst,
 (b) a fluidization gas inlet located below the distributor for producing a fluidized bed of the solid catalyst above the distributor,
 (c) an atomizer nozzle located above the distributor and at the bottom of the fluidized bed, the nozzle being fed an inert atomization gas and a liquid mixture of the alcohol and/or ether and the feedstock, and
 (d) a transesterified reaction product gas outlet located above the fluidized bed.

18. The system of claim 17, wherein the fluidization gas is carbon monoxide and/or dioxide, nitrogen, argon, water vapour, or a mixture of oxygen and nitrogen.

19. The system of claim 17, further comprising an inert cooling gas inlet located between the fluidized bed and below the product gas outlet.

20. The system of claim 17, further comprising a quench connected to the product gas outlet to collect the transesterified reaction product.

* * * * *